United States Patent
Britsch et al.

(10) Patent No.: US 6,551,512 B1
(45) Date of Patent: Apr. 22, 2003

(54) CONTINUOUS METHOD FOR SEPARATING SUBSTANCES ACCORDING TO MOLECULAR SIZE

(75) Inventors: Lothar Britsch, Reute (DE); Michael Schulte, Rüsselsheim (DE); Jochen Strube, Hagen (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 09/857,975

(22) PCT Filed: Dec. 4, 1999

(86) PCT No.: PCT/EP99/09495

§ 371 (c)(1),
(2), (4) Date: Jun. 13, 2001

(87) PCT Pub. No.: WO00/37156

PCT Pub. Date: Jun. 29, 2000

(30) Foreign Application Priority Data

Dec. 19, 1998 (DE) .......................... 198 58 892

(51) Int. Cl.[7] ............................... B01D 15/08
(52) U.S. Cl. ................ 210/635; 210/659; 210/198.2
(58) Field of Search ................ 210/635, 656, 210/659, 198.2

(56) References Cited

U.S. PATENT DOCUMENTS

| 5,434,299 A | * | 7/1995 | Negawa | 210/659 |
| 5,465,748 A | * | 11/1995 | Bowers | 137/240 |
| 5,630,943 A | * | 5/1997 | Grill | 210/659 |
| 5,939,565 A | * | 8/1999 | Jumppanen | 549/418 |
| 5,968,362 A | * | 10/1999 | Russo | 210/635 |
| 6,063,284 A | * | 5/2000 | Grill | 210/659 |
| 6,293,999 B1 | * | 9/2001 | Cheng | 95/96 |

FOREIGN PATENT DOCUMENTS

| DE | 4316136 | 11/1994 | ................. 210/659 |
| WO | 9734918 | 9/1997 | ................. 210/656 |

OTHER PUBLICATIONS

Snyder, Introduction to modern liquid chromatography John Wiley, 1979, pages 484,485, and 663.*

* cited by examiner

Primary Examiner—Ernest G. Therkorn
(74) Attorney, Agent, or Firm—Millen, White, Zelano & Branigan, P.C.

(57) ABSTRACT

Continuous separation methods, in partricular using SMB methods, are disclosed, in which the analytes are separated by size exclusion chromatography (gel permeation chromatography).

9 Claims, 5 Drawing Sheets

CONTINUOUS METHOD FOR SEPARATING SUBSTANCES ACCORDING TO MOLECULAR SIZE

REFERENCE TO RELATED APPLICATIONS

This application is a 371 of PCT/EP99/09495 filed Dec. 4, 1999.

The invention relates to the application of chromatographic separation methods by the size exclusion principle (size exclusion chromatography; SEC) to continuous chromatography methods, in particular to simulated moving bed (SMB) chromatography.

The separation of substances, in particular macromolecules, by molecular size is a widespread chromatographic separation principle. Particularly in the purification of peptides and proteins, methods such as size exclusion chromatography (SEC), frequently also referred to as gel permeation chromatography, are widely employed. Thus, for example, the review article by G. Subramanian, Process scale liquid chromatography (VCH Weinheim 1995), describes preparative applications of this separation method. However, all these applications are based on batch methods, which are distinguished by a poor space-time yield. The cause is firstly the long retention times of the components, which necessitate a long cycle time (time between two injections). Since most of the materials employed in SEC have only low pressure stability, it is not possible to increase the flow rates in order to achieve faster separation. In addition, most carrier materials have poor roadability (<5% of the gel volume). Some of these problems can be improved by the use of continuous methods. However, it has hitherto been impossible to apply these SEC separation methods to continuous procedures; the parameters for a continuous separation method of this type would have to be determined by suitable model calculations. In addition, the process parameters obtained must allow stable continuous operation.

Continuous chromatographic methods, such as, for example, simulated moving bed (SMB) chromatography, are traditionally employed on a large scale in the petrochemical and sugar industries. In the meantime, however, these methods have also been used in the fine chemical and pharmaceutical industries, principally for the separation of isomers and enantiomers, i.e. for separation problems of classical two-component mixtures. Initial attempts to isolate components from multicomponent mixtures have also been described.

In order to obtain suitable process parameters for SMB chromatography, a number of simulation models have been developed, of which the rigorous SMB process model has the most far-reaching approach. Simulation approaches have been disclosed, for example, by Nicoud et al. (Nancy, 1993) and in WO 97134 918. It is common to these methods that adsorption isotherms are determined for the analytes; these measurement results then form the basis of the model calculations. In recent further developments, model separations of binary mixtures have been demonstrated on the basis of the true counter current model: G. Storti et al. (1993) AIChE Journal 39, pages 471–472 and by E. Francotte et al. (1998) J. Chromatogr. A 796, pages 239–248. In a further development, the parameters have been optimised starting from a first parameter set using detailed process simulation: J. Strube, U. Altenhöner, M. Meurer and H. Schmidt-Traub (1997) Chem.-Ing. Tech. 69, pages 328–331, and dissertation by J. Strube (University of Dortmund, 1996). However, all these models are based on the determination of adsorption isotherms.

While the chromatographic separation methods used hitherto for SMB methods, for example enantiomer separation or ion exchange chromatography, are based on adsorptive processes, SEC is based on a completely different principle: for analytes of different molecular size, different volumes are available owing to the pore size distribution in the sorbent; larger molecules thus elute earlier than small ones. SEC is thus based on a diffusive mechanism with inclusion of a size exclusion mechanism, with no adsorption of the analytes by the sorbent. There are consequently no phase equilibriums as in adsorption chromatography. The modelling methods which supply the parameters for SMB chromatography that were known hitherto thus cannot be used for SEC. In particular, the problem arises of stabilising the raffinate front of the component retained the shortest in the region of section IV, i.e. between the raffinate and eluent lines. This problem is increased further since in many SEC separation methods, part of the analytes is eluted in the void volume. Such components are transported through zone IV and contaminate the extract component. It has hitherto been impossible to apply the process parameters from batch computer models to continuous separation methods (for example SMB separation methods) for SEC separation methods, and thus specifically to obtain separation parameters for continuous separation methods which allow stable operation.

The object of the invention is thus to develop models and methods which allow separation parameters for continuous separation methods which enable stable operation to be obtained specifically for SEC separation methods.

The invention relates to continuous separation methods, particularly using SMB methods, in which the analytes are separated by size exclusion chromatography (gel permeation chromatography).

Figure 2:
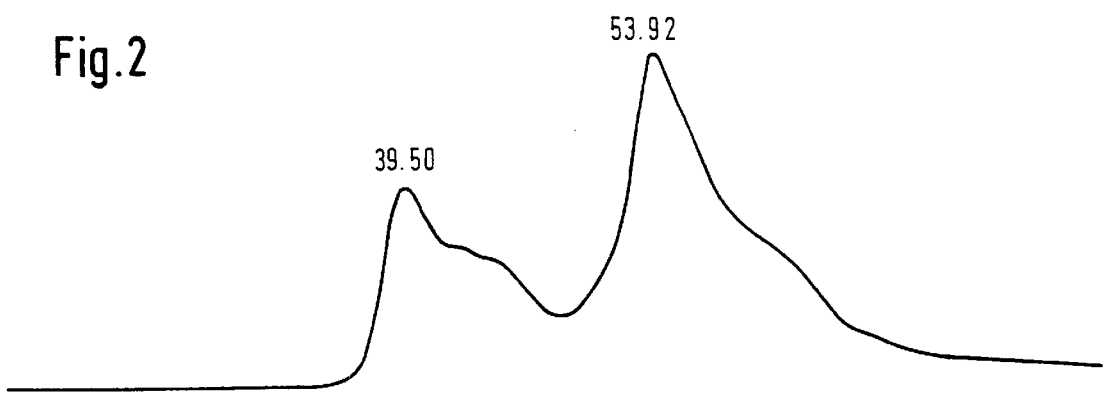
FIGS. 2–4 show the chromatograms of the individual components.
Figure 3:
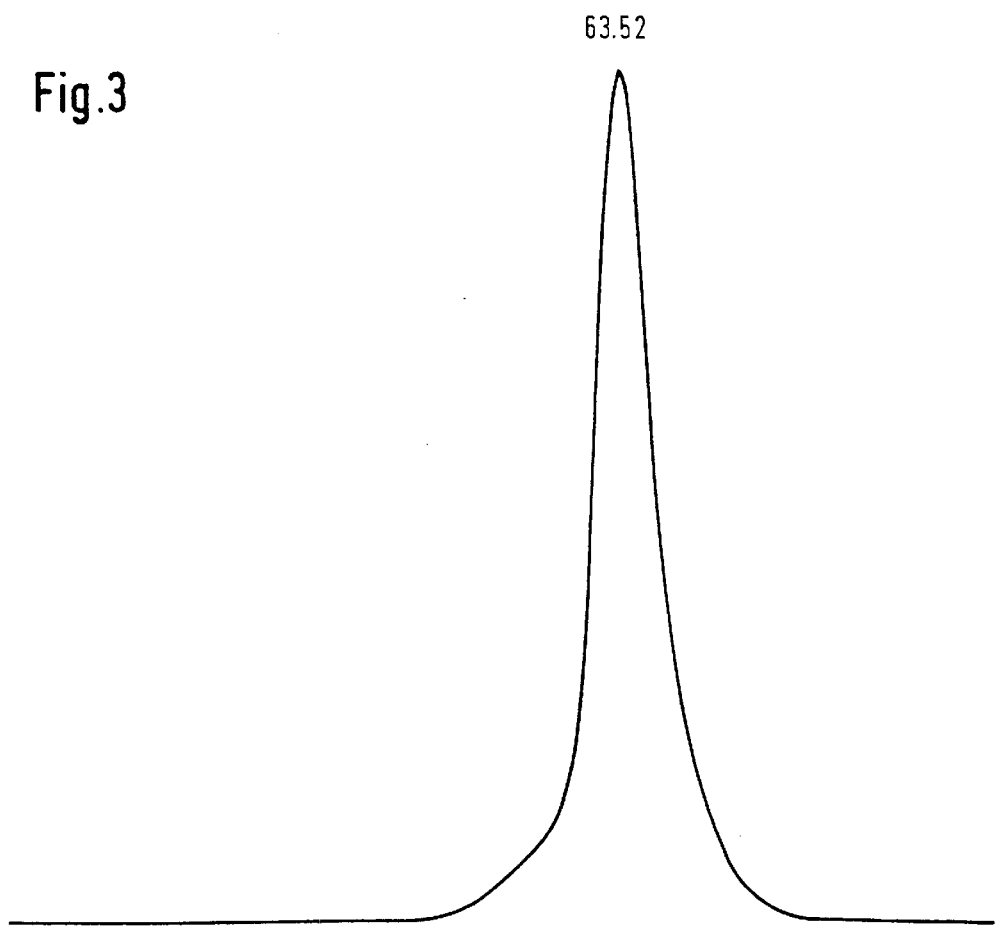
Figure 4:
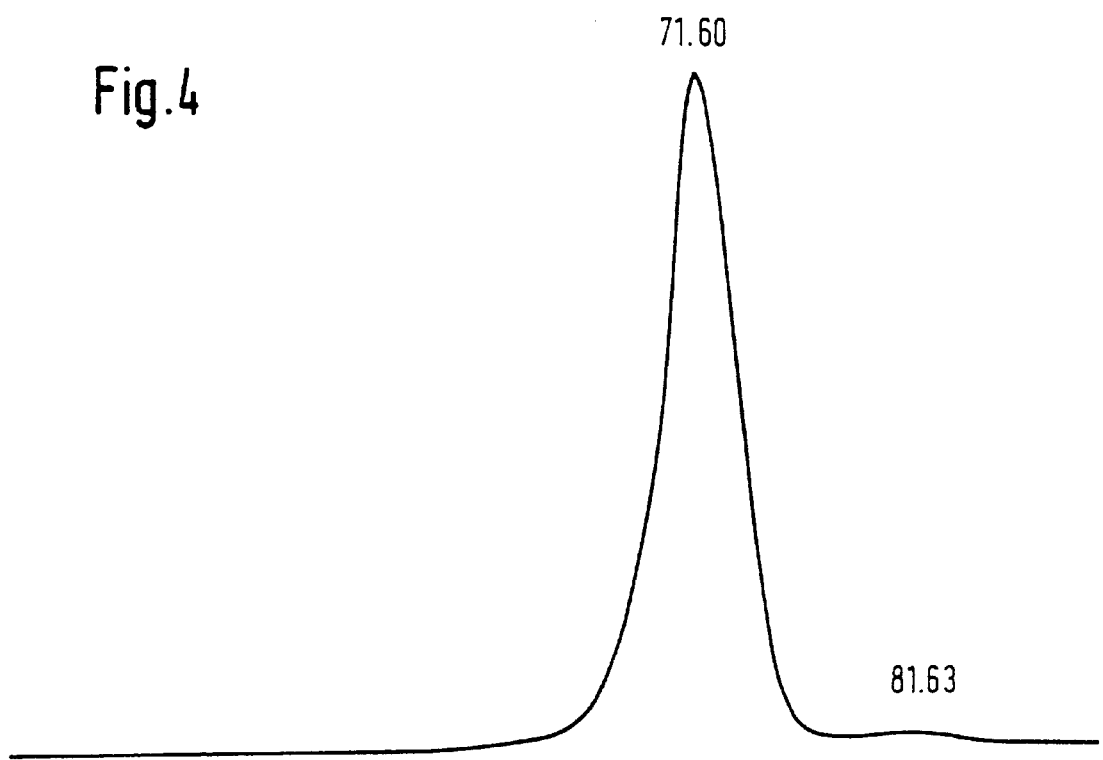

| FIG. 2 | casein fraction | RT 39.5; 53.92 min |
| --- | --- | --- |
| FIG. 3 | β-lactoglobulin A | RT 63.52 min |
| FIG. 4 | alpha-lactalbumin | RT 71.60 min |

Figure 5:
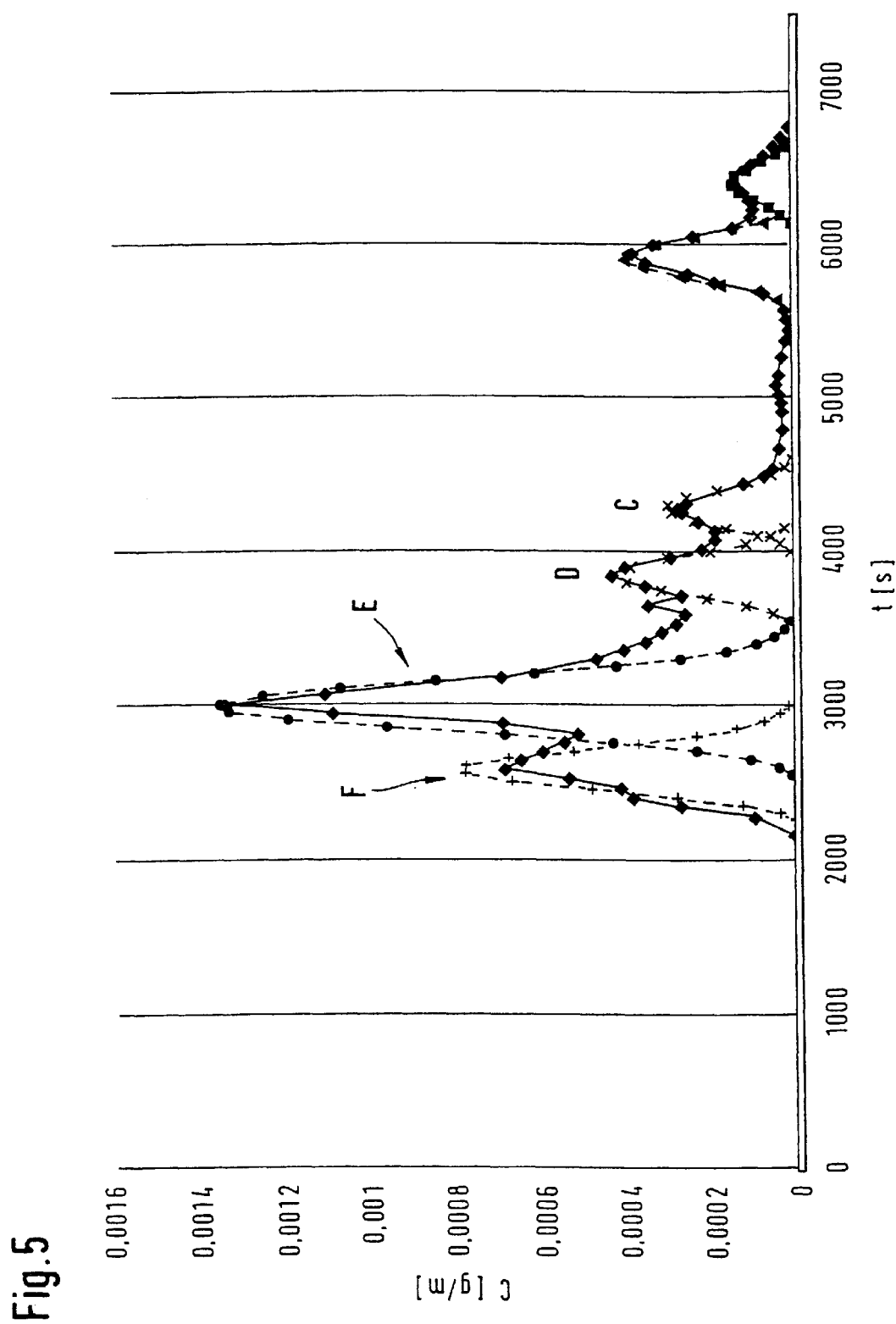

FIG. 5 shows an elution chromatogram of the individual components determined as the result of the rigorous modelling of the individual substances in accordance with the invention.

Figure 6:
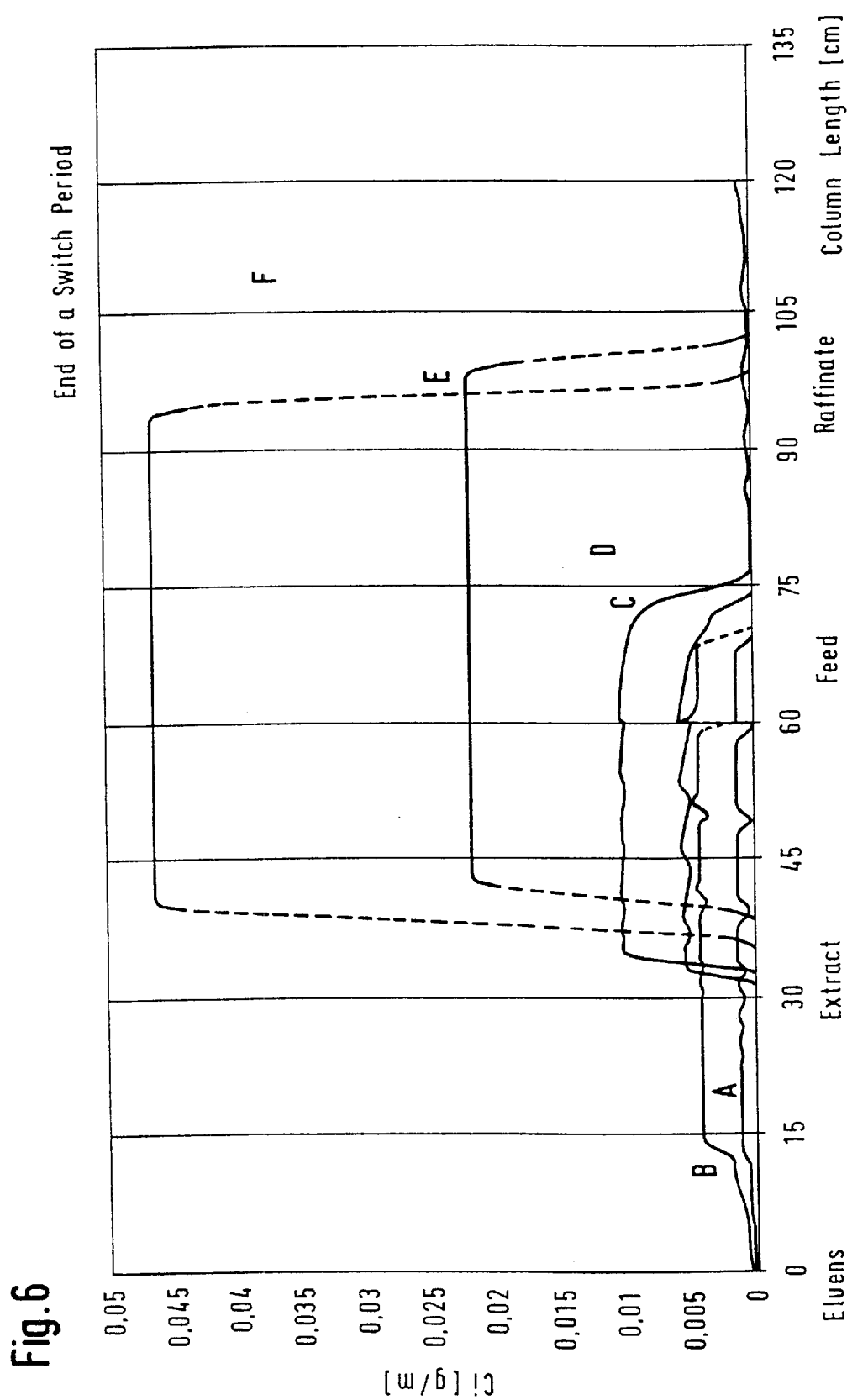

FIG. 6 shows the internal axial concentration profile of an SEC/SMB unit with the concentrations of the individual components in the individual zones at the end of a cycle time.

DESCRIPTION OF THE PREFERRED EMBODIMENTS

A theoretical model calculation for simple component systems for SEC 10 separations in the batch method has been described by Tien Gu (Mathematic Modelling of Liquid Chromatography; Springer Verlag, 1995).

It has been found that stable process parameters for use of SEC separations in SMB methods can be obtained if the following procedure is followed in accordance with invention:

a) The residence times in the separation column of the substances to be separated and the band broadening of the substance peaks are calculated. The residence times are calculated using, for example, the above-mentioned method indicated by Tien Gu (1995).

b) The data obtained by means of (analytical) batch chromatograms are used to calculate the effective porosities of each component and the residence times.

c) The band broadening can be calculated, for example, from the effective molecular diffusion coefficients. The effective molecular diffusion coefficients can be estimated on the basis of the Stokes-Einstein relation and the molecular weights of the components.

d) The agreement of the calculated data (steps b) & c)) with the observed elution profile is checked and if necessary the matching of the calculated data to the experimental data is improved in further iteration steps.

e) The requisite net flow rate ratios of the SMB process are calculated from the parameters of the matched model calculation by methods which are known in principle, as indicated, for example, in the above-mentioned publications G. Storti et al. (1993) and the dissertation by Strube (1996).

The above-mentioned procedure for the calculation of residence time and band broadening and the resultant parameters enable the previously known models (G. Storti et al. (1993) and the dissertation by Strube (1996)) to be used even without determination of adsorption isotherms.

The proposed model proved to be sufficiently accurate when checked for various concentrations and linear velocities on an individual column. The distribution of the residence times is determined here by the diffusion parameters, as apply for the internal volumes of the sorbent particles. The effective molecular diffusion coefficients are estimated from the molecular weights of the components in accordance with the Stokes-Einstein relation and taken into account in the model as material transport coefficients.

Generally known SEC carriers can be used in accordance with the invention; preference is given to pressure-stable SEC carriers, which are likewise commercially available, for example Fraktogel® EMD BioSEC, as disclosed in DE 43 16 136.

SMB units as are likewise commercially available are used in accordance of the invention. These are, for example, units constructed by connecting two-way valves or units having a multiport valve. The separation is carried out under isocratic conditions and can thus be automated in a simulated moving bed system.

In the isolation of components from multicomponent mixtures, components which elute first or last can be taken off directly in pure form. For the isolation of substances which are flanked on both sides by impurities, purification can be achieved by a combination of a plurality of SMB purification steps, as disclosed, for example, in WO 97/34 918.

In order to meet the special requirements presented by biotechnological problems to the process for multicomponent separation, the so-called open mode of operation with 3 zones without closure of the circuit flow is particularly suitable for removing large-molecular-size impurities or accumulations from the process if the low-molecular-weight fraction is to be obtained, and also for taking off large-molecular-size products directly.

In order to meet CIP (cleaning in place) requirements, operation with purging of columns in zone 1 or 4 (with the functions adsorbent regeneration and desorbent cleaning) and rinsing as well as regeneration and cleaning of the adsorbent and also sections of the piping parts and components with, for example, NaOH is crucial for operability and for avoiding accumulations.

The separation method according to the invention allows improved separation of proteins by molecular size, since it can be carried out continuously and fully automatically in large units; these separation methods can be used, in particular, in the following areas of application:

purification of proteins from transgenic animal milk;

purification of proteins, for example factors VIII, vW and IX, from blood plasma;

purification of plasmids;

a further large-volume method is the desalination of feed mixes, whose economy is improved by a continuous SEC method.

In so-called drug targeting, the aim is to convey drugs specifically to the site of action. To this end, use is made, inter alia, of drug-loaded liposomes. A problem in the preparation of these liposomes is removal of non-included drug from the loaded liposomes. This can be achieved on a large-scale by a continuous SEC method.

In addition to fractionation of natural macromolecules, the method can of course also be applied to synthetic polymers, for example polyethylene oxides, silicones, etc.

In combination with a reactive carrier, as employed in reactive SMB, reaction and separation can be carried out in a single step. A conceivable application is the removal of TAG units from recombinant proteins by a protease and simultaneous removal of TAG units from the target proteins by SEC/SMB.

Methods according to the invention are furthermore suitable for depleting viruses from biological products, removing endotoxins, particularly in aggregated form, or purifying viruses.

Further possible applications arise from the variation in the pore size distribution of the carriers used. For example, systems with fine-pored gels can be employed for the purification of peptides, such as, for example, insulin.

Even without further details, it is assumed that a person skilled in the art will be able to utilise the above description in the broadest scope. The preferred embodiments and examples should therefore merely be regarded as a descriptive disclosure which is not limiting in any way.

The complete disclosure content of all applications, patents and publications mentioned above and below is incorporated into this application by way of reference.

USE EXAMPLE

Figure 1:
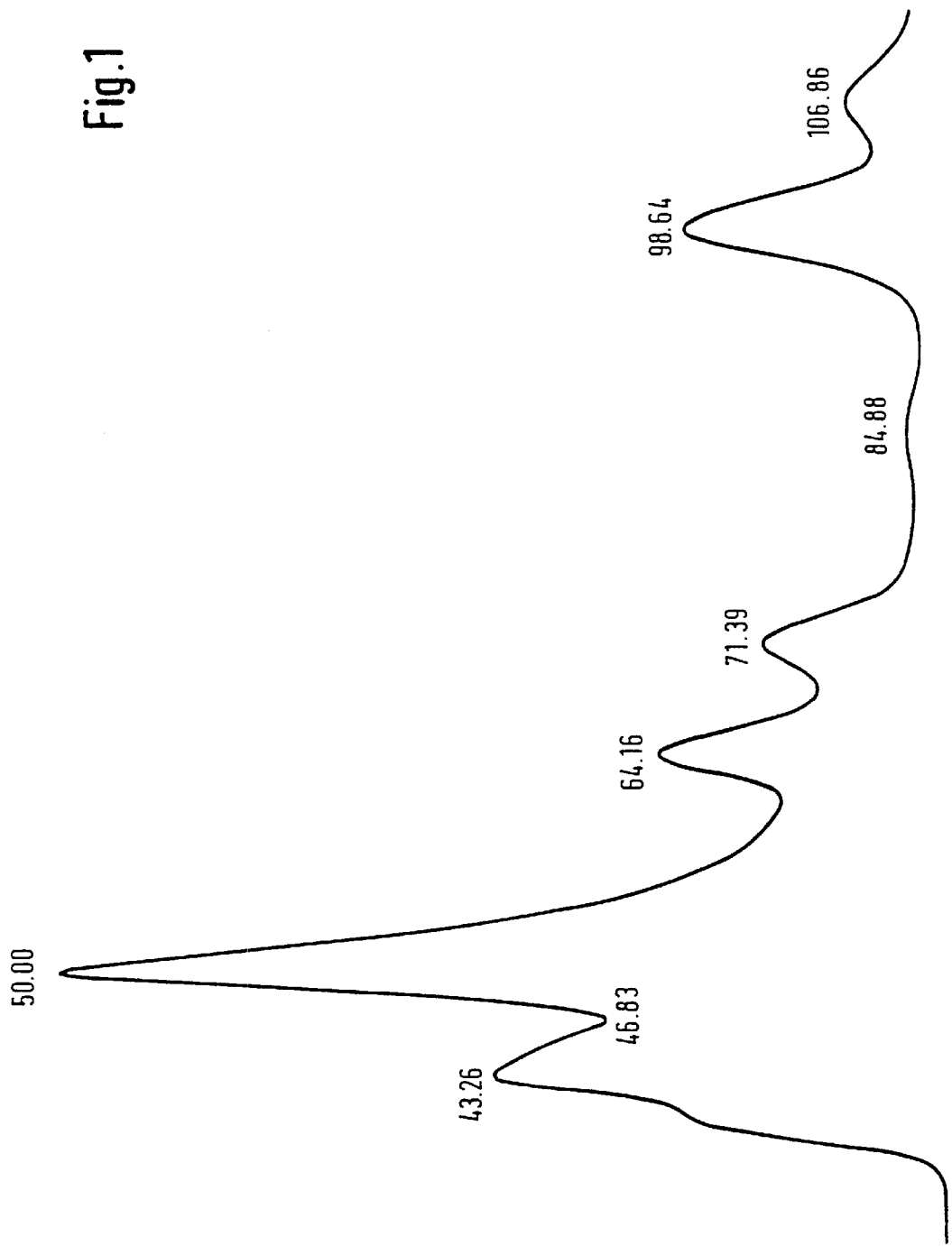
FIG. 1 shows the SEC separation of skimmed milk powder on a 600*16 mm Superformance® column packed with Fractogel® EMD BioSEC (S)

The removal of the casein fraction from skimmed milk powder is described: for the determination of the process parameters, the sample and the principal individual components are batch chromatographed: FIG. 1 shows the SEC separation of skimmed milk powder on a 600*16 mm Superformance® column packed with Fractogel® EMD BioSEC (S), and FIGS. 2–4 show the chromatograms of the individual components:

| FIG. 2 | casein fraction | RT 39.5; 53.92 min |
| FIG. 3 | β-lactoglobulin A | RT 63.52 min |
| FIG. 4 | alpha-lactalbumin | RT 71.60 min |

FIG. 5 shows an elution chromatogram of the individual components determined as the result of the iterations in the rigorous modelling of the individual substances that is proposed in accordance with the invention.

FIG. 6 shows the internal axial concentration profile of an SEC separation in an SMB unit with the concentrations of the individual components in the individual zones at the end of a cycle time. The process parameters were determined by the method according to the invention.

| Component | Retention time | |
|---|---|---|
| A | 106.86 | |
| B | 98.64 | |
| C | 71.39 | α-Lactalbumin |
| D | 64.16 | β-Lactoglobulin |
| E | 50.00 | Casein |
| F | 43.26 | Casein |

An SMB unit with the following parameters is capable of producing components E and F (casein) and A–D in purities of >99%:

| Process parameters | |
|---|---|
| Column diameter | 26 mm |
| Column length | 150 mm |
| Number of columns | 8 |
| Segmentation | 2:2:2:2 |
| Flow rates: | |
| Internal rate zone | 2.7 ml/min |
| Eluent | 1.506 ml/min |
| Extract | 1.578 ml/min |
| Feed | 0.84 ml/min |
| Feed concentration | 100 mg/ml |
| Cycle time | 21 min |

| Comparison of batch methods with SMB methods according to the invention: | | |
|---|---|---|
| Parameter | Batch | SMB |
| Column diameter | 26 mm | 26 mm |
| Column length | 600 mm | 150 mm |
| Number of columns | 1 | 8 |
| Total column volume | 319 cm$^3$ | 637 cm$^3$ |
| Feed concentration | 100 mg/ml | 100 mg/ml |
| Feed flow rate | — | 0.84 ml/min |
| Injection volume | 200 µl | — |
| Cycle time | 120 min | — |
| Feed throughput/day | 0.636 g/d | 120.96 g/d |
| Productivity (g of feed throughput/d*L column volume) | 1.99 g/d*L | 189.9 g/d*L |
| Eluent consumption (ml/g of feed) | 723.6 ml/g | 17.78 ml/g |
| Performance comparison Productivity | 1 | 95.43 |
| Performance comparison Eluent consumption | 40.69 | 1 |

A comparison of the productivities of batch and SMB methods shows the large advantage of the continuous countercurrent method owing to the much more economic utilisation of the stationary phrase:

In contrast to adsorptive separation mechanisms, no phrase equilibrium isotherms are described in accordance with invention, but instead the first time for continuous methods, the different diffusion rates into the sorbent particles, which are characteristic of component separation by the SEC method, and the different available pore volumes are used as parameters. Both parameters, which are characteristic of the separation effects of SEC separation methods, are for the first time taken into account realistically in the model on which the invention is based.

What is claimed is:

1. A method comprising continuous countercurrent chromatographic separation of analytes wherein the analytes are separated by size exclusion chromatography with no adsorption of the analytes by a sorbent, said separation being based upon calculating net flow ratios of a simulated moving bed method from parameters of checked, calculated effective porosities, residence times; and band broadening, thereby allowing stabilization of a raffinate front of the component retained the shortest in the region of Section IV.

2. A method according to claim 1, wherein the chromatography is by simulated moving bed chromatography.

3. A method according to claim 2, further comprising:

calculating separation column residence times of separated substances and band broadening of substance peaks;

obtaining data of batch chromatograms;

calculating effective porosities of each separated substance and residence times from the data;

estimating effective molecular diffusion coefficients from Stokes-Einstein relation and molecular weights of the separated substances;

calculating band broadening from the effective molecular diffusion coefficients;

checking the agreement of the calculated effective porosities, residence times, and band broadening with an observed elution profile, and optionally, improving matching of the calculated and experimental data by at least one iteration step; and calculating net flow rate ratios of the simulated moving bed method from parameters of the checked, calculated effective porosities, residence times, and band broadening.

4. A method according to claim 2, further comprising conducting the method with units wherein the units are connected by a two-way or multiport valve.

5. A method according to claim 2, wherein the separation is conducted under isocratic conditions.

6. A method according to claim 1, wherein the analytes are separated by diffusion with no sorbent adsorption.

7. A method according to claim 1, for purifying proteins from transgenic animal milk, proteins from blood plasma, plasmids, salts from feed mixes, loaded liposomes, peptides, or viruses.

8. A method according to claim 1, further comprising conducting the method with eight columns, wherein each column has a diameter of 26 mm and a length of 150 mm.

9. A method according to claim 1, wherein the size exclusion chromatography is gel permeation chromatography.

* * * * *

UNITED STATES PATENT AND TRADEMARK OFFICE
CERTIFICATE OF CORRECTION

PATENT NO. : 6,551,512 B1
DATED : April 22, 2003
INVENTOR(S) : Lothar Britsch et al.

It is certified that error appears in the above-identified patent and that said Letters Patent is hereby corrected as shown below:

Column 6,
Line 19, change "times;" to -- times, --;
Line 29, after "data" insert -- by means --.

Signed and Sealed this

Seventeenth Day of August, 2004

JON W. DUDAS
*Acting Director of the United States Patent and Trademark Office*